(12) United States Patent
Sumiyoshi et al.

(10) Patent No.: US 8,437,004 B2
(45) Date of Patent: May 7, 2013

(54) DETECTION APPARATUS

(75) Inventors: Yuhei Sumiyoshi, Utsunomiya (JP);
Takumi Tokimitsu, Moka (JP);
Hiroyuki Yuuki, Utsunomiya (JP)

(73) Assignee: Canon Kabushiki Kaisha (JP)

( * ) Notice: Subject to any disclaimer, the term of this patent is extended or adjusted under 35 U.S.C. 154(b) by 255 days.

(21) Appl. No.: 12/908,405

(22) Filed: Oct. 20, 2010

(65) Prior Publication Data

US 2011/0109908 A1 May 12, 2011

(30) Foreign Application Priority Data

Nov. 12, 2009 (JP) ................................. 2009-259310

(51) Int. Cl.
*G01N 21/55* (2006.01)
*G01N 21/88* (2006.01)

(52) U.S. Cl.
USPC ........................................ 356/445; 356/237.1

(58) Field of Classification Search .................. 356/402, 356/407, 417, 425, 445–448, 237.1–237.5; 362/296.07, 347, 516
See application file for complete search history.

(56) References Cited

U.S. PATENT DOCUMENTS

| | | | | |
|---|---|---|---|---|
| 3,702,395 A | * | 11/1972 | Rosendahl | 362/263 |
| 4,918,583 A | * | 4/1990 | Kudo et al. | 366/268 |
| 5,634,704 A | * | 6/1997 | Shikama et al. | 353/31 |
| 6,788,404 B2 | * | 9/2004 | Lange | 356/237.2 |
| 8,125,426 B2 | * | 2/2012 | Nagase et al. | 345/87 |
| 2003/0191393 A1 | | 10/2003 | Ridder et al. | |
| 2004/0141161 A1 | * | 7/2004 | Hibi et al. | 353/99 |
| 2007/0058246 A1 | | 3/2007 | Westphal et al. | |
| 2009/0257024 A1 | | 10/2009 | Luther et al. | |

FOREIGN PATENT DOCUMENTS

| | | |
|---|---|---|
| JP | 3-235010 A | 10/1991 |
| JP | 10-221242 A | 8/1998 |
| JP | 2007-133435 A | 5/2007 |
| JP | 2007-163358 A | 6/2007 |
| JP | 2008-286530 A | 11/2008 |

OTHER PUBLICATIONS

Extended European Search Report issued in corresponding EP 10188359.3 dated May 4, 2011.

* cited by examiner

*Primary Examiner* — Hoa Pham
(74) *Attorney, Agent, or Firm* — Rossi, Kimms & McDowell LLP

(57) ABSTRACT

A detection apparatus which illuminates a sample and detects light reflected by the sample, comprises a light source, a columnar reflecting member having a columnar reflecting surface which reflects light having entered a first end of the columnar reflecting member by a plurality of number of times, and emits the light from a second end of the columnar reflecting member, a mirror which reflects light radiated by the light source so as to guide to the first end and a detector, wherein the sample is illuminated with the light emitted from the second end, and the detector is configured to detect the light which has been reflected by the sample and has passed through the columnar reflecting member, and a reflecting surface of the mirror is a concave surface, and a shape of a reflecting surface of the mirror on a section perpendicular to an axis of the columnar reflecting member is concave.

13 Claims, 8 Drawing Sheets

FIG. 5A
FIG. 5B
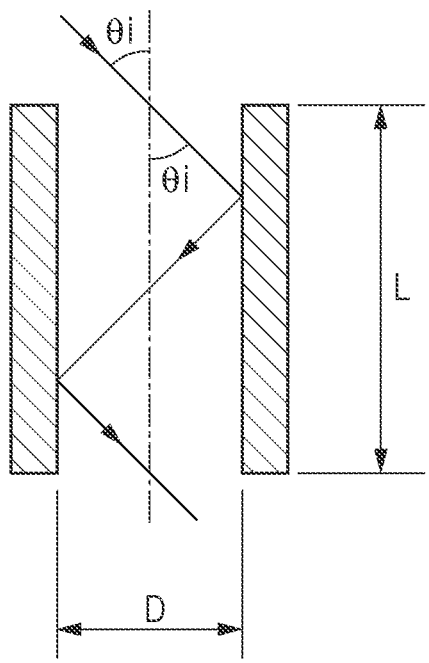
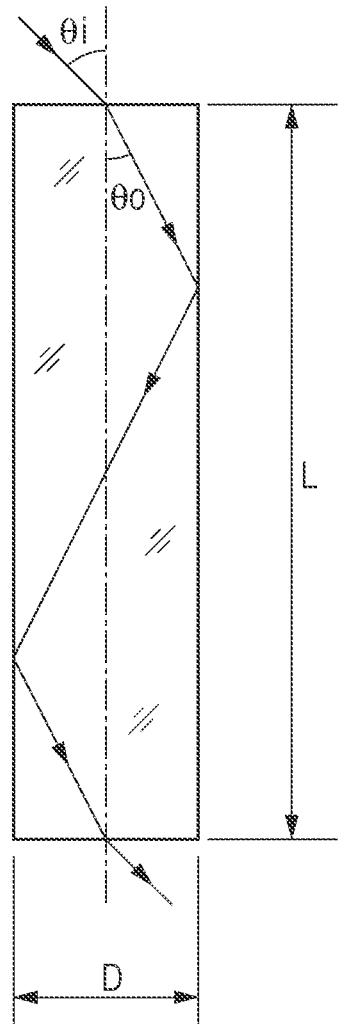

FIG. 6

| z | r |
|---:|---:|
| 11.311 | 5.082 |
| 10.860 | 5.431 |
| 10.390 | 5.761 |
| 9.901 | 6.072 |
| 9.393 | 6.364 |
| 8.866 | 6.637 |
| 8.321 | 6.892 |
| 7.757 | 7.128 |
| 7.173 | 7.344 |
| 6.571 | 7.542 |
| 5.951 | 7.722 |
| 5.311 | 7.882 |
| 4.652 | 8.023 |
| 3.975 | 8.146 |
| 3.279 | 8.250 |

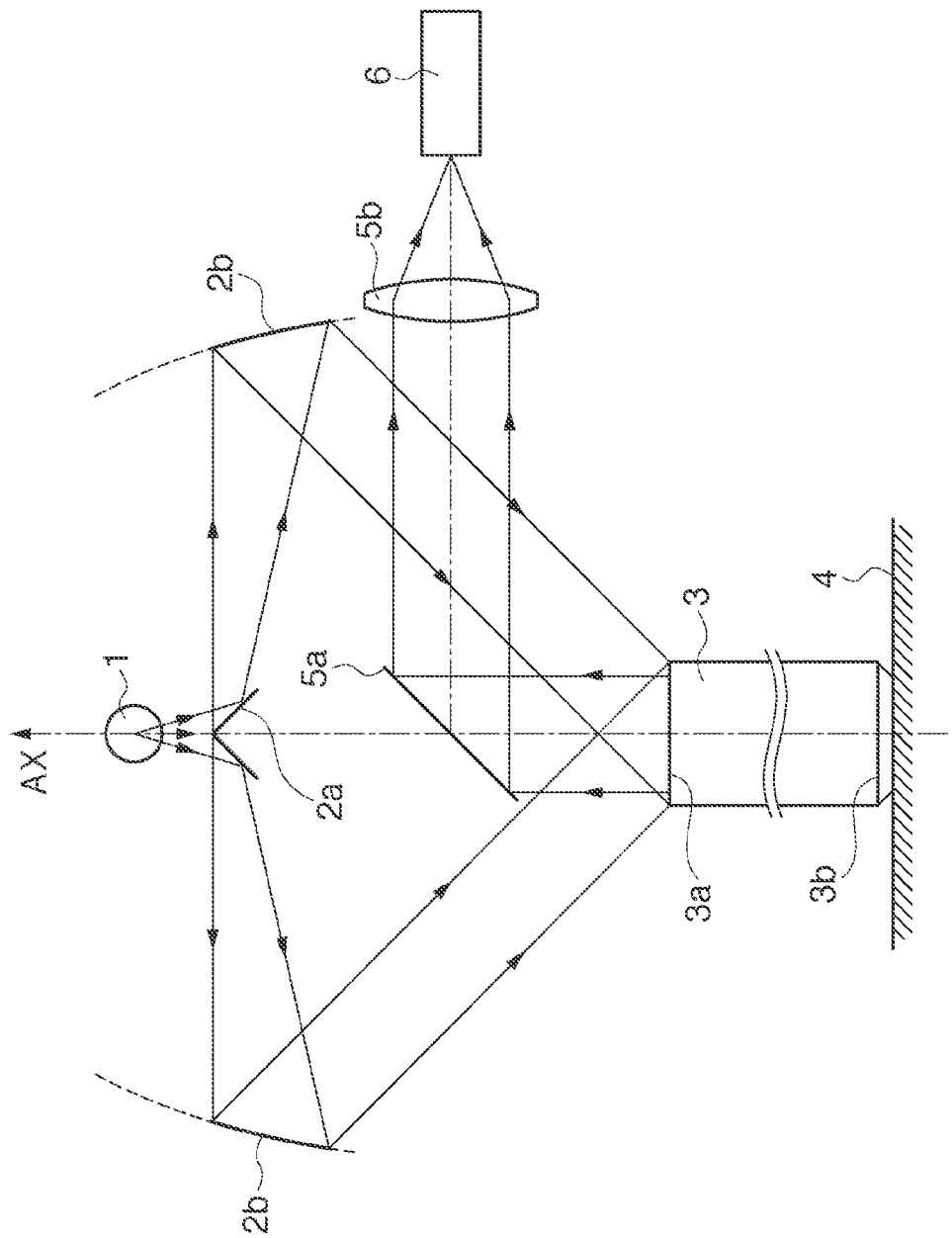

DETECTION APPARATUS

BACKGROUND OF THE INVENTION

1. Field of the Invention

The present invention relates to a detection apparatus that illuminates a sample and detects light reflected by the sample.

2. Description of the Related Art

In measurement of the reflection characteristic of a sample, an optical condition for illumination and observation, called geometry, greatly affects the measurement result, so a geometry suited to a sample is adopted. For example, 45/0 geometry (45° illumination-vertical light receiving) is employed when measuring a printed product. Since directional illumination is done for such geometries, an illumination apparatus is required to illuminate a measurement sample with light from a specific direction (Japanese Patent Laid-Open No. 2008-286530). Japanese Patent Laid-Open No. 2008-286530 proposes an illumination apparatus for two 45° directions.

However, a conventional directional illumination system has difficulty in obtaining high illuminance distribution uniformity while illuminating a sample from all directions. If the number of illumination directions is small, accurate measurement fails under the influence of the installation direction of a sample, rotation, or the like. When the entire measurement region cannot be illuminated with a uniform illuminance distribution, no accurate measurement can be done under strong influence of a portion having high illuminance in the measurement region. As a method of uniforming the illuminance distribution while implementing omni-directional illumination, a method using an integrating sphere, and the like are known. However, the use of the integrating sphere decreases the efficiency of light use.

SUMMARY OF THE INVENTION

The present invention provides a technique advantageous for obtaining a uniform illuminance distribution while illuminating a sample from more directions.

One of the aspects of the present invention provides an apparatus which illuminates a sample and detects light reflected by the sample, comprising a light source, a columnar reflecting member having a columnar reflecting surface which reflects light having entered a first end of the columnar reflecting member by a plurality of number of times, and emits the light from a second end of the columnar reflecting member, a mirror which reflects light radiated by the light source so as to guide to the first end, and a detector, wherein the sample is illuminated with the light emitted from the second end, and the detector is configured to detect the light which has been reflected by the sample and has passed through the columnar reflecting member, and a reflecting surface of the mirror is a concave surface, and a shape of a reflecting surface of the mirror on a section perpendicular to an axis of the columnar reflecting member is concave.

Further features of the present invention will become apparent from the following description of exemplary embodiments with reference to the attached drawings.

BRIEF DESCRIPTION OF THE DRAWINGS

FIGS. 5A and 5B are views for explaining a preferable length of the columnar reflecting member;

FIG. 6 is a table exemplifying data of the reflecting surface of a mirror;

FIG. 8 is a view showing a detection apparatus according to the third embodiment of the present invention.

DESCRIPTION OF THE EMBODIMENTS

Embodiments of the present invention will now be described with reference to the accompanying drawings.

Figure 1A:
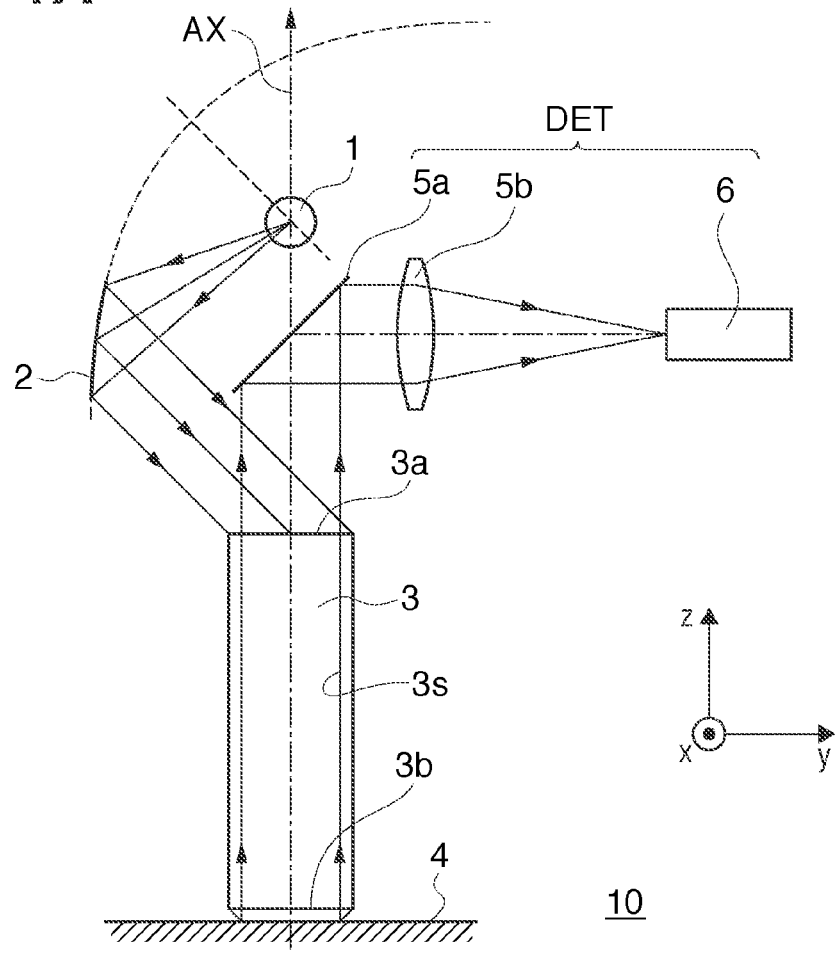
FIGS. 1A and 1B are views showing a detection apparatus according to the first embodiment of the present invention.
Figure 1B:
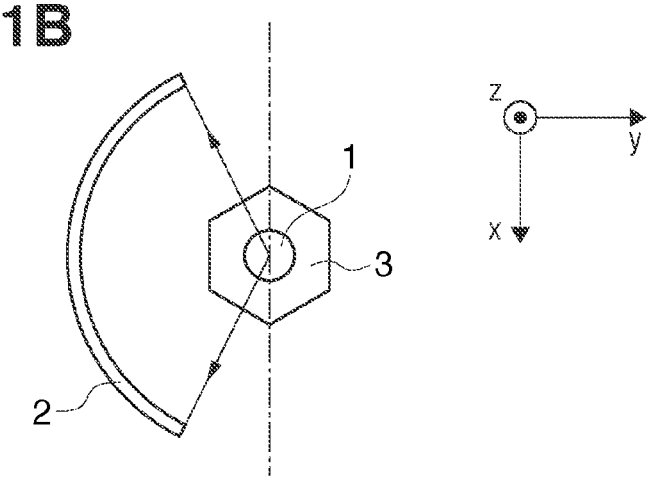

A detection apparatus 10 according to the first embodiment of the present invention will be described with reference to FIGS. 1A and 1B. The detection apparatus 10 can be used to measure the reflection characteristic of a sample 4. The detection apparatus 10 illuminates the sample 4 and detects light reflected by it. The detection apparatus 10 includes a light source 1, columnar reflecting member 3, mirror 2, and detector DET. The columnar reflecting member 3 has a columnar reflecting surface 3s which reflects light having entered a first end 3a by a plurality of number of times, and emits it from a second end 3b. The columnar reflecting surface is a reflecting surface which has a constant sectional shape and extends along an axis AX perpendicular to the section. The columnar reflecting member is a member having a columnar reflecting surface. The mirror 2 reflects light radiated by the light source 1 so as to guide to the first end 3a of the columnar reflecting member 3. The detection apparatus 10 illuminates the sample 4 with light emerging from the second end 3b of the columnar reflecting member 3. The light is reflected by the sample 4 and passes through the columnar reflecting member 3. The detector DET detects the light having passed through the columnar reflecting member 3. In the first embodiment, the detection apparatus 10 is configured to measure a reflection characteristic in so-called 45/0 geometry.

As the light source 1, a Xe lamp, halogen lamp, LED, or the like is available. When measuring the color of the sample 4, a light source which emits beams having wavelengths in the entire visible light range can be employed. In 45° illumination, the mirror 2 can be configured to reflect light radiated by the light source 1 in a direction having an angle of 45° with respect to the axis AX of the columnar reflecting member 3. The reflecting surface of the mirror 2 can take a paraboloidal surface shape having a focus at the position of the light source 1, and an axis of symmetry inclined by 45° from the axis AX. The reflecting surface of the mirror 2 on a plane including the axis AX can take a parabolic shape which has a focus at the position of the light source 1 and is inclined by 45° from the axis AX. The reflection surface of the mirror 2 is a concave surface, and the shape of the reflecting surface of the mirror 2 on a section perpendicular to the axis AX can be a concave shape, for example, arcuate shape with respect to the axis AX.

The mirror 2 having this structure can converge, to the first end of the columnar reflecting member 3, light diverging from the light source widely in the x and y directions. As a result, light emitted by the light source 1 can be used efficiently. Since light entering the columnar reflecting member 3 contains light components in various directions, a uniform illuminance distribution and omni-directional illumination can be easily implemented. The open angle of the columnar reflecting member 3 on the x-y plane can be set to 120°, as exemplified in FIGS. 1A and 1B, but may be another angle. Especially when a lamp with poor directivity is employed as the light source 1, the nearby light source 1 radiates light in all directions. In this case, it is also effective to form the mirror 2 into a ring shape.

Instead of arranging the light source 1 at the focus of the mirror 2, it is also possible to arrange the light source 1 at a position spaced apart from the focus and guide light emitted by the light source 1 to the focal position along a light guide optical system such as an optical fiber. This arrangement is excellent in increasing the degree of freedom of the arrangement of the component or reducing the influence of exhaust heat from the light source 1.

The columnar reflecting member 3 is a columnar light-transmitting member or a member having a columnar hollow region. The columnar reflecting member 3 is arranged so that its axis AX becomes perpendicular to the surface of the sample 4 or a sample table (table on which the sample 4 is placed). In 45° illumination, light enters the first end 3a of the columnar reflecting member 3 in a direction having an angle of 45° with respect to the axis AX. The light emerges from the second end 3b of the columnar reflecting member 3 in a direction having an angle of 45° with respect to the axis AX, illuminating the sample 4. The light incident on the sample 4 is reflected and scattered by the surface of the sample 4. Of the light components, one in a 0° direction (direction parallel to the axis AX) enters the second end 3b of the columnar reflecting member 3, and emerges from the first end 3a without being reflected by the columnar reflecting surface 3s.

The detector DET detects the light emerging from the columnar reflecting member 3. The detector DET can include, for example, a deflecting mirror 5a which deflects the optical path of light emerging from the columnar reflecting member 3, a condenser lens 5b, and an analyzer 6. The analyzer 6 may include, for example, a spectrometer. The analyzer 6 may also include a processor which processes spectral distribution data obtained by the spectrometer.

Figure 2:
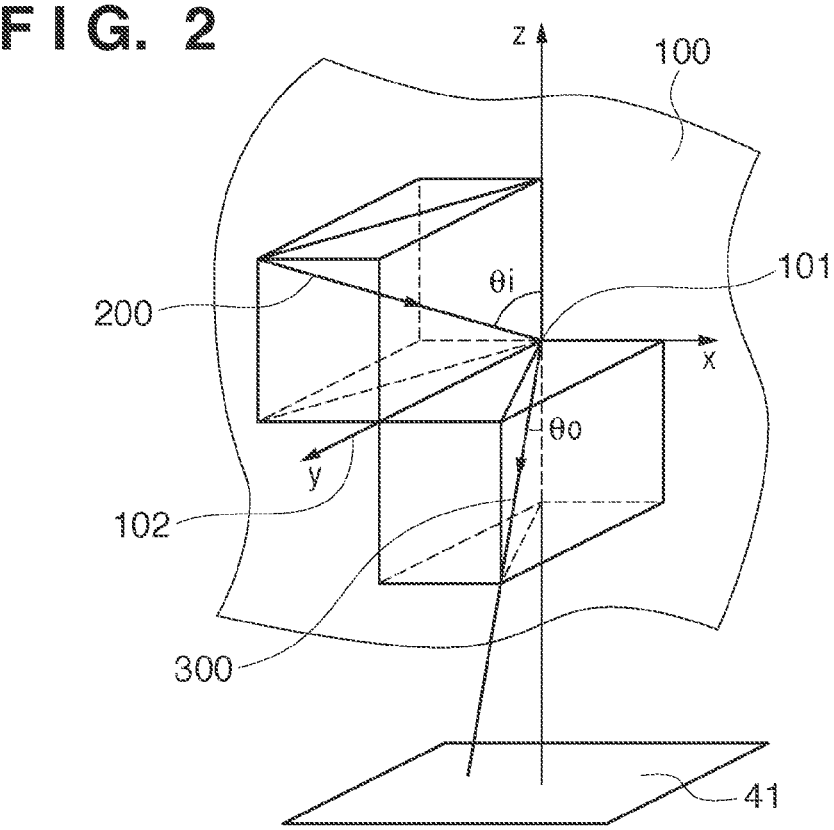
FIG. 2 is a view for explaining the optical effect of a columnar reflecting member.

The optical effect of the columnar reflecting member 3 will be explained with reference to FIG. 2. A small region 41 on the surface of the sample 4 is assumed, and the z-axis is defined parallelly to the normal. Assume that a beam 200 is reflected at a point 101 on a curved surface 100, and reaches the small region 41 as a beam 300. At this time, a normal 102 of the curved surface at the point 101 is assumed to be parallel to the small region 41 and is defined as the y-axis. Further, the x-axis is defined in a direction perpendicular to the y- and z-axes. Then, reflection of the beam at the point 101 on the curved surface 100 can be given by a relationship as indicated by two rectangular parallelepipeds in FIG. 2. In this case, the angles θi and θo of the incident beam 200 and reflected beam 300 with respect to the z-axis (angles with respect to the small region 41) become equal to each other. In other words, the angle of the beam with respect to the sample surface is preserved before and after reflection when the beam is reflected by a surface whose normal is parallel to the sample surface. For this reason, the first embodiment employs the columnar reflecting member 3 having a shape with only a normal parallel to the sample surface, that is, the columnar reflecting surface 3s. In repetitive reflection of a beam by the columnar reflecting surface 3s, the angle of the beam with respect to the sample surface is preserved, and the beam is reflected in various directions in directions (x- and y-axis directions in FIG. 2) parallel to the sample surface. Accordingly, the illuminance distribution is uniformed, and the sample can be illuminated from many directions, that is, substantially all directions.

Figure 3:
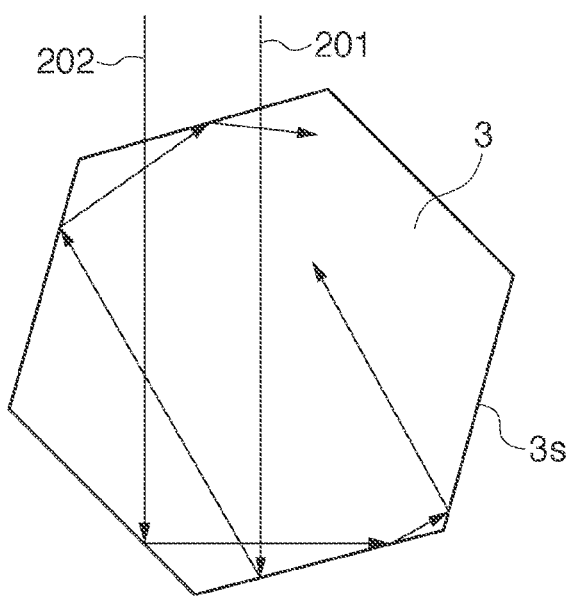
FIG. 3 is a view showing a light stirring effect by the columnar reflecting member.

FIG. 3 is a view showing a state in which two parallel beams enter a hexagonal columnar reflecting member 3 and are reflected by the columnar reflecting surface 3s when viewed from the first end 3a. As a result of reflecting two beams 201 and 202 by a plurality of number of times by the columnar reflecting surface 3s of the columnar reflecting member 3, the beams 201 and 202 lose their original parallel relationship and are deflected in directions different from the original ones. The effect of reflecting light in various directions within a plane parallel to the sample surface will be called a light stirring effect.

Figure 4A:
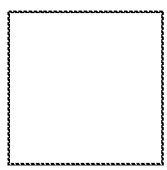
FIGS. 4A to 4G are views exemplifying the sectional shape of the columnar reflecting member.
Figure 4B:
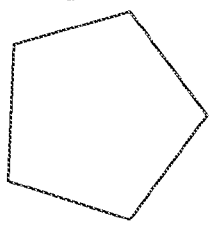
Figure 4C:
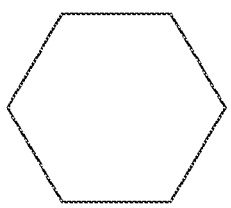

The light stirring effect depends on the sectional shape of the columnar reflecting surface 3s. FIGS. 4A to 4E exemplify the sectional shape of the columnar reflecting surface 3s. FIGS. 4A, 4B, and 4C show columnar reflecting surfaces 3s with polygonal columnar shapes, that is, quadrangular, pentagonal, and hexagonal columnar shapes. The light stirring effect is high for a shape having a smaller number of sides and more dissimilar to the column. Each of the columnar reflecting members 3 having the columnar reflecting surfaces 3s with the sectional shapes in FIGS. 4A, 4B, and 4C may be formed from a columnar member made of a light-transmitting material and have its outer surface as a reflecting surface. Alternatively, the columnar reflecting member 3 may be formed from a member having a columnar hollow region and have its inner surface as a reflecting surface.

Figure 4D:
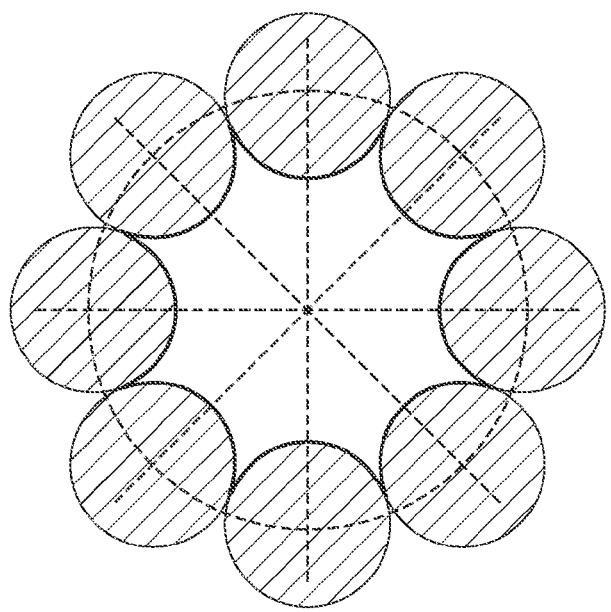
Figure 4F:
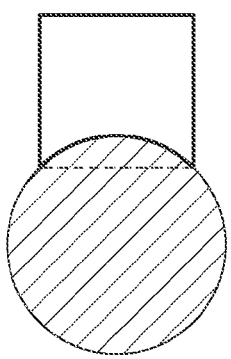
Figure 4E:
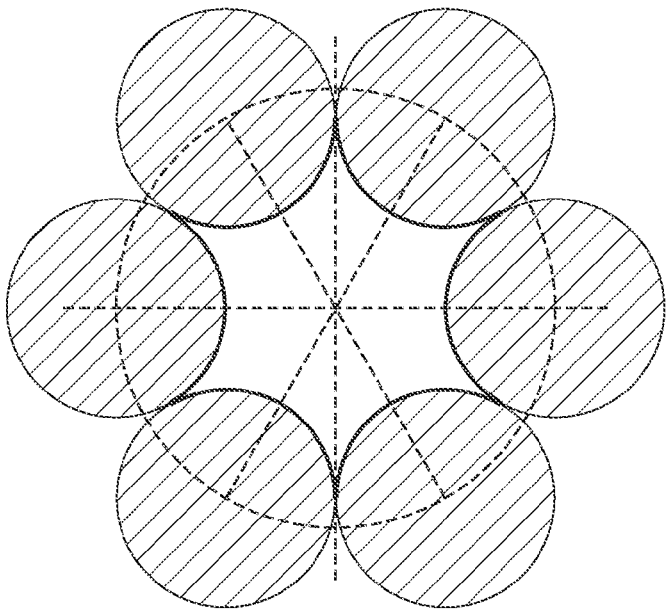

FIGS. 4D and 4E show examples in each of which cylindrical reflecting members are combined to form a hollow structure and a portion (indicated by a thick line) facing the inner space serves as a reflecting surface. These structures contain curved surfaces and can reflect an incident beam in various directions. Hence, the examples of FIGS. 4D and 4E achieve higher stirring effects than those in the examples of FIGS. 4A, 4B, and 4C. The shapes exemplified in FIGS. 4D and 4E will be called crown-like columnar shapes.

Figure 4G:
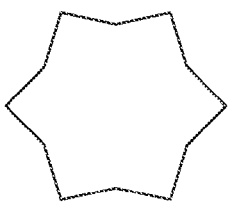

In the example shown in FIG. 4F, flat and curved surfaces are combined. By forming part of a polygon into a curved surface, a higher stirring effect than that of a simple polygon can be obtained. As exemplified in FIG. 4G, a jagged polygonal sectional shape may be adopted.

The length of the columnar reflecting member 3 will be examined. FIGS. 5A and 5B are sectional views of the columnar reflecting member 3 when taken along a plane perpendicular to the sample surface. FIG. 5A exemplifies a hollow columnar reflecting member. FIG. 5B exemplifies a columnar reflecting member made of a transmitting material. To satisfactorily obtain the light stirring effect, a beam entering the columnar reflecting member 3 is desirably reflected twice or more by the inner wall of the rod. As shown in FIGS. 5A and 5B, a beam entering the columnar reflecting member is desirably reflected at least once by each of opposite reflecting surfaces and then emerges from the columnar reflecting member 3. Hence, the minimum length of the columnar reflecting member 3 (more accurately, the columnar reflecting surface 3s) necessary for this purpose is obtained. First, for a hollow columnar reflecting member as exemplified in FIG. 5A, letting D be the typical diameter of the columnar reflecting surface and θi be the incident angle of a beam, the necessary length L is given by $L = 2D/\tan\theta i$ in FIG. 5A. To the contrary, for a columnar reflecting member made of a transmitting material as exemplified in FIG. 5B, letting D be the typical diameter of the columnar reflecting surface, n be the refractive index of the columnar reflecting member, and θi be the incident angle of a beam, the necessary length L is given by $L = (2D/\sin\theta i) \times \sqrt{1-(\sin\theta i/n)^2}$. This equation is given by the Snell's law: $\sin\theta o = n \times \sin\theta i$. To obtain a satisfactory light stirring effect, the length of the columnar reflecting surface is desirably set equal to or larger than L.

In 45/0 geometry, the incident angle of light to the columnar reflecting member 3 need not be strictly 45° in general. For example, the JIS standard permits a beam at an angle of 8° or less with respect to the center line (45°). According to this, the incident angle to the columnar reflecting member can be set to 45°±8°. Even in this case, the property of preserving the angle of light on the columnar reflecting member 3 is maintained, so even the angle of light on the sample surface similarly becomes 45°±8°.

A method of manufacturing a columnar reflecting member will be exemplified. For a polygonal hollow columnar reflecting member, it suffices to prepare and combine a plurality of flat reflecting members. The flat reflecting member can be fabricated by polishing glass to be flat and coating it with a highly reflective film. For a crown-like hollow columnar reflecting member, it suffices to prepare and combine a plurality of cylindrical reflecting members. The cylindrical reflecting member can be fabricated by polishing glass into a cylindrical shape and coating it with a highly reflective film. A columnar reflecting member with a shape as shown in FIG. 4F can also be fabricated by the same method. In contrast, for a columnar reflecting member made of a transmitting material, fabrication of a crown-like columnar shape is difficult, while that of a polygonal columnar shape is easy. The polygonal columnar reflecting member made of a transmitting material can be fabricated by polishing glass into a polygonal columnar shape. A highly reflective coating can be applied to the side surface of the columnar reflecting member made of a transmitting material. Note that an antireflection coating on the second end 3b can reduce the influence of multiple reflection between the sample surface and the second end 3b on measurement.

The distance between the columnar reflecting member and the sample surface can be set to an appropriate short interval. A long distance between the columnar reflecting member and the sample surface may cause a blur around the illumination region, decreasing the illuminance distribution uniformity. Measurement may be done by bringing the columnar reflecting member into press contact with the sample surface, or at an interval of about several mm. When the interval of about several mm is set, it suffices to shield the surrounding blurred portion from light by a field stop or the like.

Figure 9A:
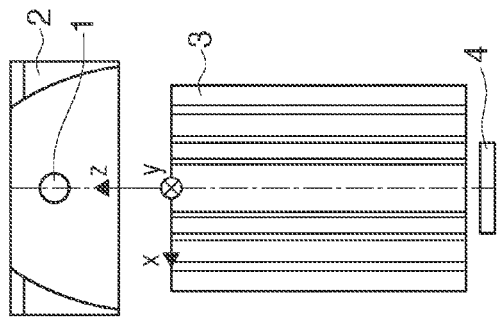
FIGS. 9A to 9D are views showing a more concrete example of the detection apparatus according to the first embodiment of the present invention.
Figure 9C:
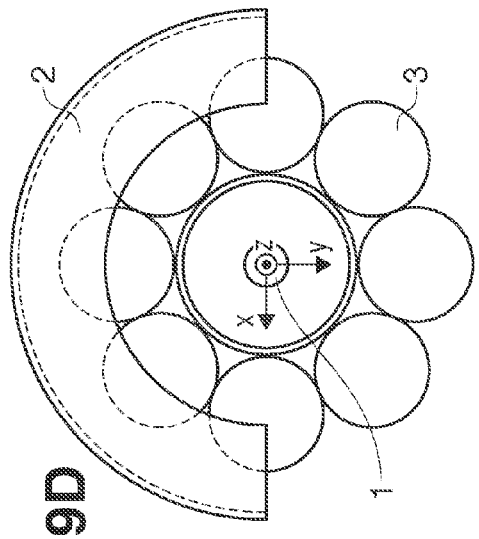
Figure 9B:
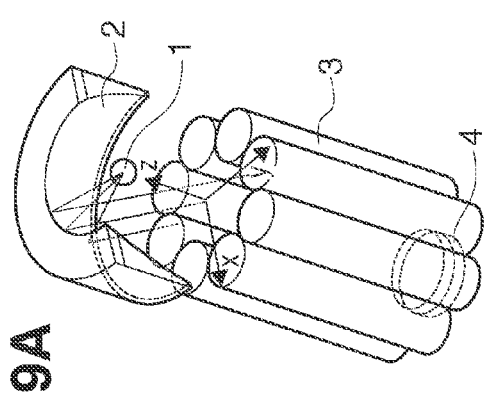
Figure 9D:
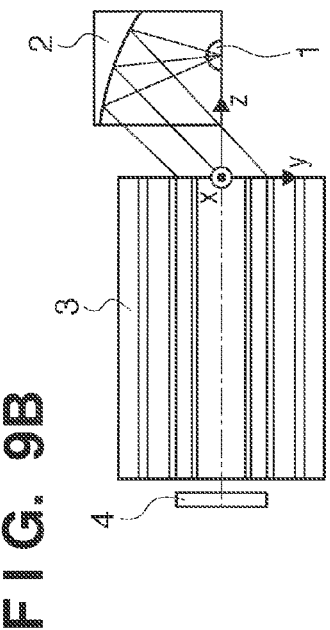

FIGS. 9A to 9D are views showing a more concrete example of the first embodiment. FIG. 9A is a bird's-eye view, FIG. 9B is a side view, FIG. 9C is a front view, and FIG. 9D is a top view. In this example, the columnar reflecting member 3 is a crown-like hollow columnar reflecting member. Eight 3.8-mmϕ cylinders are arranged to circumscribe a 6.2-mmϕ circle. The material of the cylinder is a reflecting material such as glass. Since the cylinder surface is used as a reflecting surface, a highly reflective coating is applied. The light source 1 is an exit end for light which is emitted by a light-emitting element (not shown) such as a lamp at another location and is guided along an optical fiber. The light is radiated with directivity having a spread of about 0.5 in NA (Numerical Aperture). FIG. 6 shows shape data of the mirror 2. The mirror 2 is rotationally symmetrical about the axis (z-axis in FIGS. 9A to 9D) of the columnar reflecting member 3. In FIG. 6, z is a z-coordinate value in the x-y-z coordinate system using the upper end face (first end) of the columnar reflecting member 3 as a reference, and r is the radius of the reflecting surface of the mirror 2 at the z-coordinate value. Of these shape data, those at a z-coordinate value of 3.5 (inclusive) to 11.0 (inclusive) can be used for the mirror 2. The sample 4 can be arranged at a distance of about 1 mm from the lower end (second end) of the columnar reflecting member 3. The detector (not shown) arranged above the light source 1 detects, of reflected/scattered beams traveling from the sample 4, those in a direction perpendicular to the sample 4, and measures, for example, reflection characteristics.

Figure 7:
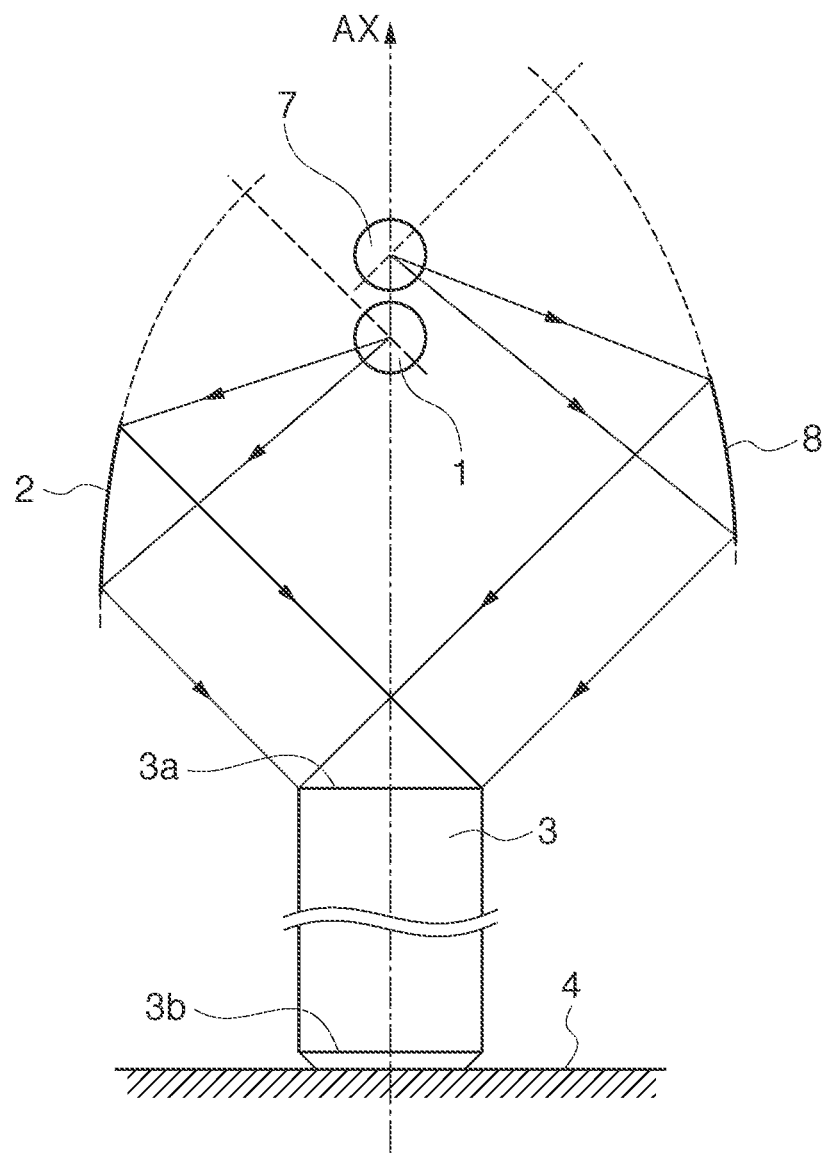
FIG. 7 is a view showing a detection apparatus according to the second embodiment of the present invention.

A detection apparatus 11 according to the second embodiment of the present invention will be described with reference to FIG. 7. The same reference numerals as those in FIGS. 1A and 1B showing the first embodiment denote the same parts. For illustrative convenience, FIG. 7 does not show a detector DET, but the detection apparatus 11 can include the detector DET similar to that in the first embodiment. The detection apparatus 11 in the second embodiment is also a 45/0 geometry detection apparatus.

The detection apparatus 11 in the second embodiment includes a second light source 7 and second mirror 8 in addition to a first light source 1 and first mirror 2. The second mirror 8 can be configured to reflect light radiated by the second light source 7 in a direction having an angle of 45° with respect to the axis AX of a columnar reflecting member 3. The reflecting surface of the second mirror 8 can take a paraboloidal surface shape having a focus at the position of the second light source 7, and an axis of symmetry inclined by 45° from the axis AX. The reflecting surface of the second mirror 8 on a plane including the axis AX can take a parabolic shape having a focus at the position of the second light source 7 and an axis of symmetry inclined by 45° from the axis AX. The reflecting surface of the second mirror 8 is a concave surface and the shape of the reflecting surface of the second mirror 8 on a section perpendicular to the axis AX can be a concave shape, for example, arcuate shape with respect to the axis AX.

In this arrangement, one detection apparatus 11 can handle the two light sources 1 and 7. The two light sources 1 and 7 allow the following application. For example, one light source serves as a visible light source, and the other serves as an ultraviolet source. In this case, the color of a sample can be measured using the visible light source, and the fluorescent characteristic of the sample can be measured using the ultraviolet source. That is, one detection apparatus can perform colorimetry and fluorimetry. Also, the two light sources can be used as follows. A combination of the two light sources can obtain a good spectrum in the entire visible light range. For example, as for an LED, even a white LED has a wavelength band where the spectrum intensity is low, and is not good for use in colorimetry. In this case, a plurality of LEDs can be combined to compensate for each other, ensuring a sufficient spectrum intensity in the entire visible light range. It suffices to configure the light sources in this way, turn them on simultaneously, and measure a reflection characteristic. Two identical light sources may be used and turned on simultaneously. In this case, the light quantity increases, shortening the time taken for measurement.

A detection apparatus 12 according to the third embodiment of the present invention will be described with reference to FIG. 8. The same reference numerals as those in FIGS. 1A and 1B showing the first embodiment denote the same parts. For illustrative convenience, FIG. 8 does not show a detector DET, but the detection apparatus 12 can include the detector DET similar to that in the first embodiment. The detection apparatus 12 in the third embodiment is also a 45/0 geometry detection apparatus.

The detection apparatus 12 in the third embodiment includes a conical mirror 2a and ring-like mirror 2b. The conical mirror 2a radially deflects light emitted by a light source 1. The ring-like mirror 2b reflects, in a direction having an angle of 45° with respect to the axis AX of a columnar reflecting member 3, light which is emitted by the light source 1 and travels via the conical mirror 2a. The light then enters a first end 3a of the columnar reflecting member 3. The reflecting surface of the mirror 2b can take a paraboloidal surface shape having a focus at the position of the light source 1, and an axis of symmetry inclined by 45° from the axis AX. The reflecting surface of the mirror 2 on a plane including the axis AX can take a parabolic shape having a focus at the position of the virtual image of the light source 1 that is formed by the conical mirror, and an axis of symmetry inclined by 45° from the axis AX. The shape of the reflecting surface of the mirror 2 on a section perpendicular to the axis AX can be a circle. This arrangement allows light to enter the columnar reflecting member 3 from all directions. Together with the light stirring effect by the columnar reflecting member 3, a uniform illuminance distribution and 45° illumination from all directions can be implemented. In this case, light enters the first end (light-entering end face) of the columnar reflecting member 3 from all directions. Thus, the rod length necessary to uniform the illuminance distribution can be set relatively short.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-259310, filed Nov. 12, 2009, which is hereby incorporated by reference herein in its entirety.

What is claimed is:

1. An apparatus which illuminates a sample and detects light reflected by the sample, the apparatus comprising:
    a light source;
    a columnar reflecting member having a columnar reflecting surface which reflects light having entered a first end of the columnar reflecting member, and emits the light from a second end of the columnar reflecting member to illuminate the sample;
    a mirror which reflects light radiated by the light source to guide the light reflected by the mirror to the first end; and
    a detector configured to detect the light which has been reflected by the sample and has passed through the columnar reflecting member without being reflected by the columnar reflecting member,
    wherein a reflecting surface of the mirror is a concave surface, and
    wherein a shape of a reflecting surface of the mirror on a section perpendicular to an axis of the columnar reflecting member is concave.

2. The apparatus according to claim 1, wherein the shape of the reflecting surface of the mirror on the section is an arcuate shape.

3. The apparatus according to claim 1, wherein the shape of the reflecting surface of the mirror on the section is an arcuate shape centered on the axis.

4. The apparatus according to claim 1, wherein the shape of the reflecting surface of the mirror on the section perpendicular to the axis is a ring shape.

5. The apparatus according to claim 1, further comprising:
    a second light source; and
    a second mirror which reflects light radiated by the second light source to guide the light reflected by the second mirror to the first end.

6. The apparatus according to claim 5, wherein a reflecting surface of the second mirror is a concave surface, and a shape of the reflecting surface of the second mirror on a section perpendicular to the axis is concave.

7. The apparatus according to claim 5, wherein the light source and the second light source radiate lights having wavelength bands different from each other.

8. The apparatus according to claim 1, further comprising a second mirror which reflects light radiated by the light source to guide the light reflected by the second mirror to the mirror.

9. The apparatus according to claim 8, wherein a reflecting surface of the second mirror is a concave surface, and a shape of the reflecting surface of the second mirror on a section perpendicular to the axis is concave.

10. The apparatus according to claim 1, wherein the columnar reflecting surface includes a curved surface.

11. The apparatus according to claim 1, wherein the light reflected by the mirror enters the first end of the columnar reflecting member at a particular incident angle.

12. The apparatus according to claim 1, wherein:
    the sample is illuminated by light incident at a particular incident angle, and
    the detector detects light reflected by the sample and travelling at a particular angle.

13. The apparatus according to claim 1, wherein the apparatus illuminates the sample and detects light reflected by the sample by a 45°/0° geometry.

* * * * *